United States Patent
Lin

(10) Patent No.: US 10,835,567 B2
(45) Date of Patent: Nov. 17, 2020

(54) METHOD FOR REGULATING EXPRESSIONS OF TPH1 GENE, DDC GENE, AND/OR AANAT GENE BY USING BANANA PEEL EXTRACT

(71) Applicant: TCI CO., LTD, Taipei (TW)

(72) Inventor: Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 312 days.

(21) Appl. No.: 15/890,080

(22) Filed: Feb. 6, 2018

(65) Prior Publication Data

US 2018/0228860 A1    Aug. 16, 2018

Related U.S. Application Data

(60) Provisional application No. 62/457,457, filed on Feb. 10, 2017.

(30) Foreign Application Priority Data

Jan. 29, 2018 (TW) ............... 107103071 A

(51) Int. Cl.
*A61K 36/88* (2006.01)
*A61P 25/00* (2006.01)
*A23L 33/105* (2016.01)

(52) U.S. Cl.
CPC .............. *A61K 36/88* (2013.01); *A61P 25/00* (2018.01); *A23L 33/105* (2016.08)

(58) Field of Classification Search
CPC .......... A61P 25/00; A61P 25/20; A61K 36/88; A61K 36/18; A23L 33/105; A23V 2002/00; A23V 2200/322
See application file for complete search history.

(56) References Cited

FOREIGN PATENT DOCUMENTS

| FR | 2997301 A3 * | 5/2014 | ........... A61K 31/721 |
|---|---|---|---|
| KR | 10-2012-0095352 A | 8/2012 | |
| WO | WO 2011/018700 A1 | 2/2011 | |

OTHER PUBLICATIONS

Akamine, K; Koyama, T; Yazawa, K "Banana Peel Extract Suppressed Prostate Gland Enlargement in Testosterone-Treated Mice" Bioscience, Biotechnology and Biochemistry, Sep. 7, 2009, 73(9), pp. 1911-1914; doi: 10.1271/bbb.80770) (Year: 2009).*

Borjigin, Jimo, et al., "Diurnal variation in mRNA encoding serotonin N-acetyltransferase in pineal gland," *Nature*, vol. 378, pp. 783-785 (Dec. 1995).

Zill, Peter, et al., "Analysis of tryptophan hydroxylase I and II mRNA expression in the human brain: A post-mortem study," *Journal of Psychiatric Research*, vol. 41, pp. 168-173 (2007).

Montioli, Riccardo, et al., "A comprehensive picture of the mutations associated with aromatic amino acid decarboxylase deficiency: from molecular mechanisms to therapy implications," *Human Molecular Genetics*, vol. 23, No. 20, pp. 5429-5440 (May 27, 2014).

"Is Your Sleep Good? Do You Feel Sleepy Until Dawn?", https://kknews.cc/zh-tw/health/xzx16n9.mtnl, with English translation, 13 pages (Aug. 21, 2018).

"Banana peel is also treasure," *Epoch Times*, Jun. 1, 2018 (8 pgs.) http://www.epochtimes.com/b5/8/1/4/n1965515.htm.

"Banana peel can treat hemorrhoids," *Family Health report*, Mar. 3, 2016 (4 pgs.) http://blog.sina.com.cn/s/blog_4e75ab550102wgx7.htm.

"Don't throw it! Banana peel health benefits are three times that of pulp," *Epoch Times*, Jul. 19, 2016, (8 pgs.) http://www.epochtimes.com/b5/16/7/19/n8114568.htm.

Udenfriend, Sidney, et al., "Physiologically Active Amines in Common Fruits and Vegetables," *Archives of Biochemistry and Biophysics*, vol. 85, pp. 487-490 (1959).

Ramarkrishna, Akula, et al., "Phytoserotonin, A Review," *Plant Signaling & Behavior*, vol. 6, Issue 6, pp. 800-809, Jun. 2011.

* cited by examiner

*Primary Examiner* — Aaron J Kosar
(74) *Attorney, Agent, or Firm* — Christensen, Fonder, Dardi & Herbert PLLC

(57) ABSTRACT

A method for increasing the expressions of TPH1 gene, DDC gene and/or AANAT gene is provided. The method comprises administering to a subject in need a composition, wherein the composition comprises an effective amount of a banana peel extract. The method is effective in treating, preventing or adjusting diseases or physiological functions related to TPH1, DDC and/or AANAT genes.

8 Claims, 4 Drawing Sheets

Sleep disturbance questionnaire

Name:　　　　Age:　　　　Date:

1. Do you feel satisfied with your currently sleep condition? Note: scoring depends on option.

| 0 | 1 | 2 | 3 | 4 |
|---|---|---|---|---|
| Very satisfied | Satisfied | Moderately Satisfied | Unsatisfied | Extremely unsatisfied |

2. How was the sleep condition in the last two weeks? Note: scoring depends on option.

| | 0 | 1 | 2 | 3 | 4 |
|---|---|---|---|---|---|
| How long did it take for you to fall asleep | Very short (<15 mins) | Short (15-30 mins) | Natural (30-60 mins) | Long (>60 mins) | Very long (>90 mins) |
| Total sleep time | more than 8 hours | 7-8 hours | 6-7 hours | 5-6 hours | less than 5 hours |
| | Note: the duration from the moment of falling asleep to that of waking up the next day; the word "the moment of waking up" refers to the timepoint of starting the daily activities. | | | | |
| Did you feel tired after waking up? | Never (in good spirit) | Sort of (a little sleepy) | Natural (feel sleepy, but it does not affect the daily life) | Sever (feel very sleepy, but can be freshen up by taking something) | Very sever (feel very sleepy, and cannot be freshen up) |

3. How many times did your sleep be disturbed by the following factors? Note: scoring the total score depends on option, and then dividing the total score by the total number of problems.

| | Never | <1 time/week | 1-2 time/week | 3-4 time/week | Every day |
|---|---|---|---|---|---|
| Woke up in the midnight or early morning | 0 | 1 | 2 | 3 | 4 |
| Needed to go to the bathroom | 0 | 1 | 2 | 3 | 4 |
| Could not breath smoothly | 0 | 1 | 2 | 3 | 4 |
| Coughed or snored | 0 | 1 | 2 | 3 | 4 |
| Felt too hot | 0 | 1 | 2 | 3 | 4 |
| Felt too cold | 0 | 1 | 2 | 3 | 4 |
| Had nightmare | 0 | 1 | 2 | 3 | 4 |
| Felt pain | 0 | 1 | 2 | 3 | 4 |
| Other factors | 0 | 1 | 2 | 3 | 4 |

4. Did the sleeping problems affect your daily life?
    (a) no (0) (please answer problem 5 directly) ☐yes (please answer the following problems (b))
    (b) The daily life being affected includes:

Note: scoring the total score depends on option, and then dividing the total score by the total number of problems.

| | Seldom | Sometimes | Often | Usually |
|---|---|---|---|---|
| Felt tired often, or even doze off | 1 | 2 | 3 | 4 |
| Felt burnout often, or felt unhappy | 1 | 2 | 3 | 4 |
| Felt pain or sore without reasons | 1 | 2 | 3 | 4 |
| Could not focus, and be forgetful | 1 | 2 | 3 | 4 |

5. In the past two weeks, how many times in a week did you need to use drugs or other ways (e.g., alcohol, excise, labor...) to help fall asleep? Note: scoring depends on option.

| 0 | 1 | 2 | 3 | 4 |
|---|---|---|---|---|
| Never | <1 time/week | 1-2 time/week | 3-4 time/week | Almost every day |

FIG. 5

METHOD FOR REGULATING EXPRESSIONS OF TPH1 GENE, DDC GENE, AND/OR AANAT GENE BY USING BANANA PEEL EXTRACT

CROSS REFERENCE TO RELATED APPLICATIONS

This application claims priority to U.S. Provisional Application Ser. No. 62/457,457 filed on Feb. 10, 2017, in the United States Patent and Trademark Office, and to Taiwan Patent Application No. 10710371 filed on Jan. 29, 2018, in the Taiwan Intellectual Property Office, the disclosures of which are incorporated herein in their entirety by reference.

FIELD OF THE INVENTION

The present invention relates to the uses of banana peel extract, including the uses in treating, preventing or adjusting diseases or physiological functions related to TPH1 (Tryptophan hydroxylase 1), DDC (DOPA decarboxylase) and/or AANAT (aralkylamine N-acetyltransferase) genes. The present invention especially relates to the use of banana peel extract in increasing the expression of melatonin, thereby treating insomnia and/or ameliorating sleep disturbances.

BACKGROUND OF THE INVENTION

Melatonin, which is a hormone secreted from pineal gland and serves the function of adjusting biological clock. People can stay awake during the daytime because the secretion of melatonin is suppressed by the exposure to light. On the other hand, the secretion of melatonin will increase during the nighttime and thus people can fall asleep. The secretion of melatonin in the nighttime would be insufficient if one maintains a lifestyle of working at night or irregular shifts, being nervous, and/or using electronics for a long period of time. The insufficient secretion of melatonin will reduce the sleep quality or even cause sleep disturbances (e.g., insomnia) and/or problems (e.g., feeling tired in the daytime, messing up the biological clock, decreasing the immunity), and thus seriously affect the daily life.

Medicines generally used in clinic for treating sleep disturbance include sedative-hypnotic drugs (e.g., benzodiazepine and barbiturate) and antidepressants (e.g., clomipramine and imipramine). However, the afore-mentioned medicines are prone to cause addiction and may have side effects such as hypersomnia, nausea, headache, vomiting, gastrointestinal discomfort, memory impairment, rebound insomnia, unconsciousness, ataxia, dyspnea, and/or somnambulism. Currently, melatonin being extracted from the pineal glands of cows and/or being chemically synthesized is also commercially available, while such melatonin is strictly controlled or forbidden in the countries that have concerns about mad cow disease and/or the uncertain safe dose of melatonin. Therefore, there is necessity and urgency for continuously developing a medicine or method for treating insomnia and/or ameliorating sleep disturbances effectively without causing addictions and side effects.

Researchers have found that the expression of melatonin is regulated by genes such as TPH1 gene, DDC gene and AANAT gene, wherein an increased expression of TPH1 gene, DDC gene and/or AANAT gene is helpful for increasing the expression of melatonin and promoting the secretion of melatonin. Accordingly, insomnia and/or sleep disturbances would be effectively treated or ameliorated if the expression of TPH1 gene, DDC gene and/or AANAT gene could be increased. Inventors of the present invention found that banana peel extract is effective in increasing the expression of genes such as TPH1 gene, DDC gene and AANAT gene, and thus, can be used for treating insomnia and/or ameliorating sleep disturbances as well as for treating, preventing or adjusting diseases or physiological functions related to the above genes.

SUMMARY OF THE INVENTION

An objective of the present invention is to provide a method for increasing the expressions of TPH1 (Tryptophan hydroxylase 1) gene, DDC (DOPA decarboxylase) gene and/or AANAT (aralkylamine N-acetyltransferase) gene, comprising administering to a subject in need a composition, wherein the composition comprises an effective amount of banana peel extract. The method is for at least one of increasing the expression of melatonin, promoting the secretion of melatonin, treating insomnia, treating diseases related to neurometabolic disorder, preventing diseases related to neurometabolic disorder, ameliorating sleep disturbances, regulating appetite, regulating sleep, regulating mood, regulating vasoconstriction, regulating hemostatic function and regulating immune response. Preferably, the method is for treating insomnia and/or ameliorating sleep disturbances. In the method according to the present invention, the composition is administered to the subject by oral administration, transdermal administration, or a combination thereof.

Another objective of the present invention is to provide a use of a banana peel extract in the manufacture of a composition, wherein the composition is used for at least one of increasing the expression of TPH1 gene, increasing the expression of DDC gene and increasing the expression of AANAT gene. The composition is a pharmaceutical composition or a food composition. Preferably, the composition is used for increasing the expression of melatonin and/or promoting the secretion of melatonin.

Still another objective of the present invention is to provide a composition, which is used for increasing the expression of TPH1 gene, DDC gene and/or AANAT gene. The composition is a pharmaceutical composition or a food composition and comprises an effective amount of banana peel extract. Preferably, the composition is used for increasing the expression of melatonin and/or promoting the secretion of melatonin.

The pharmaceutical composition provided in accordance with the present invention is used for at least one of treating insomnia, treating diseases related to neurometabolic disorder, and preventing diseases related to neurometabolic disorder. Preferably, the pharmaceutical composition is used for treating insomnia. The pharmaceutical composition is provided in a form for oral administration or transdermal administration.

The food composition provided in accordance with the present invention is used for at least one of ameliorating sleep disturbances, regulating appetite, regulating sleep, regulating mood, regulating vasoconstriction, regulating hemostatic function and regulating immune response. Preferably, the food composition is used for ameliorating sleep disturbances. The food composition is a health food, a dietary supplement, a functional food, a nutritional supplement food or a special nutritional food. Preferably, the food composition is provided as dairy products, meat products, breadstuff, pasta, cookies, troche, capsule, fruit juices, teas, sport beverages or nutritional beverages.

The detailed technology and preferred embodiments implemented for the present invention are described in the following paragraphs accompanying the appended drawings for people skilled in this field to well appreciate the features of the claimed inventive.

BRIEF DESCRIPTION OF THE DRAWINGS

FIG. 5 shows a Sleep Disturbance Questionnaire.

DESCRIPTION OF THE PREFERRED EMBODIMENTS

Figure 1:
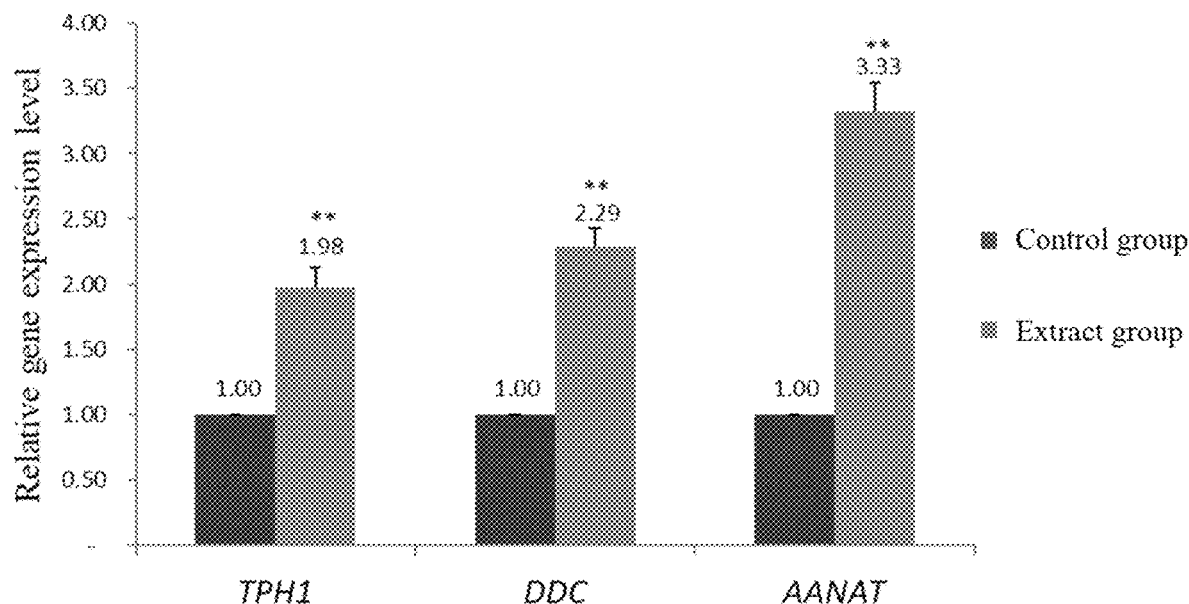
FIG. 1 shows, in comparison with those of the control group, the expression levels of TPH1 gene, DDC gene and AANAT gene in the human neuroblastoma cells of the extract group, wherein the cells in "control group" was cultured in a medium free of banana peel extract for 6 hours, and those in the "extract group" was cultured in a medium containing banana peel extract for 6 hours.

The following will describe some of the embodiments of the present invention in detail. However, without departing from the spirit of the present invention, the present invention may be embodied in various embodiments and should not be limited to the embodiments described in the specification or defined in the appended claims.

Unless otherwise indicated herein, the expressions "a," "an," "the," or the like recited in the specification of the present invention (especially in the claims) are intended to include both the singular and plural forms. The term "treat" or "treating" recited in this specification should not be construed as treating a subject until the subject is completely recovered, but should include maintaining the progression or symptoms of the diseases in a substantially static state, increasing the recovery rate of a subject, alleviating the severity of a particular condition of illness, or increasing the quality of life of a patient. The term "prevent" or "preventing" recited in this specification refers to inhibiting or preventing a particular condition of illness from breaking out, or maintaining good health in a sensitive subject to tolerate diseases. The term "regulate" or "regulating" recited in this specification refers to upregulating (includes inducing, stimulating, and enhancing) or downregulating (includes inhibiting and weakening) the physiological functions in a subject toward a normal state. The term "subject" recited in this specification refers to a mammalian, including human and non-human animals.

Banana is a perennial herb originated from the tropical and subtropical Asia. In Taiwan, banana is mainly planted in Kaohsiung, Tainan, Pingtung and Taitung. Generally, the edible portion of banana is its flesh part while its peel is discarded. Therefore, the economic value of banana will be increased if the banana peel can also be utilized.

It is known that TPH1 gene is mainly involved in the synthesis of serotonin, which is related to physiological functions such as appetite, sleep, mood, vasoconstriction, hemostatic function and immune response. Accordingly, the decreased expression of TPH1 gene will affect the above physiological functions related to serotonin. The aforementioned facts can be noted from such as "Peter Zill et. al, 2007, Analysis of tryptophan hydroxylase I and II mRNA expression in the human brain: a post-mortem study," which is entirely incorporated hereinto by reference. Therefore, if the expression of TPH1 gene can be increased, the above physiological functions related to serotonin can be regulated.

It is known that DDC gene is involved in the synthesis of melatonin, and the deficiency of DDC gene will also lead to neurometabolic disorder. The aforementioned facts can be noted from such as "Riccardo Montioli et. al, 2014, A comprehensive picture of themutations associated with aromatic amino acid decarboxylase deficiency: from molecular mechanisms to therapy implications," which is entirely incorporated hereinto by reference. Therefore, if the expression of DDC gene can be increased, the diseases related to neurometabolic disorder can be treated or prevented, and the physiological functions related to the synthesis of melatonin can be regulated.

It is known that AANAT gene plays an important role in the synthesis of melatonin. The aforementioned facts can be noted from such as "Jimo Borjigin et. al, 1995, Diurnal variation in mRNA encoding serotonin N-acetyltransferase in pineal gland," which is entirely incorporated hereinto by reference. Therefore, if the expression of AANAT gene can be increased, the physiological functions related to the synthesis of melatonin can be regulated.

Inventors of the present invention found that banana peel extract is effective in regulating the expressions of genes such as TPH1, DDC and AANAT. Accordingly, the present invention relates to the uses of the banana peel extract in increasing expression of TPH1 gene, DDC gene and/or AANAT gene, including providing a composition comprising banana peel extract, the use of banana peel extract in the manufacture of a composition, and a method comprising administering to a subject in need a composition comprising an effective amount of banana peel extract, wherein the composition can increase expression of TPH1 gene, DDC gene and/or AANAT gene.

The banana peel extract in accordance with the present invention can be provided by a method comprising the following steps: (a) extracting banana peel with an extraction solvent to provide a crude extract solution; (b) centrifuging the crude extract solution, and filtering the supernatant thus obtained to provide a filtrate; (c) concentrating the filtrate by vacuum to obtain a concentrated extract solution; and (d) drying the concentrated extract solution to obtain a dry matter.

In step (a), the extraction solvent is a polar solvent, and can optionally comprise an acid. The polar solvent can be selected from the group consisting of water, alcohol (e.g., C1-C4 alcohols) and combinations thereof. The acid can be selected from the group consisting of acetic acid, citric acid, hydrochloric acid and combinations thereof. The extraction solvent can be provided by mixing an acid with a polar solvent at a volume ratio ranging from 0.1:100 to 5:100 (acid:polar solvent). For example, the extraction solvent can be provided by mixing citric acid with water at a volume ratio ranging from 0.5:100 to 1:100 (citric acid:water). In addition, there is no limitation of the amount of extraction solvent as long as the banana peel can be evenly dispersed in the extraction solvent. For example, in step (a), the extraction solvent and the banana peel can be used at a volume ratio ranging from about 1:1 to about 20:1 (extraction solvent:banana peel). In one embodiment of the present invention, the extraction of step (a) was carried out with the use of extraction solvent and banana peel at a volume ratio of 6:1 (extraction solvent:banana peel), and the extraction solvent was provided by mixing citric acid with water at a volume ratio of 1:100 (citric acid:water).

In step (a), the extraction can be conducted for a suitable period of time depending on the extraction solvent being adopted. When the extraction solvent is provided by mixing citric acid with water at a volume ratio of 1:100 (citric acid:water) and the volume ratio of extraction solvent:banana peel is 6:1, the extraction is usually conducted for at least 0.5 hour, preferably at least 1.5 hours, and more preferably at least 2 hours. In addition, prior to or when conducting step (a), other operations such as heating, cooling, stirring, filtration and ultrasonication can be optionally performed to further enhance the extracting effect. For example, in one embodiment of the present invention, a stirring step was conducted prior to conducting step (a), and then, the step (a) was conducted at 85° C. for 0.5 hour.

In step (c), the temperature for the vacuum concentration can be optionally adjusted. For example, the vacuum concentration of step (c) can be conducted at a temperature ranging from 45 to 70° C. In one embodiment of the present invention, the vacuum concentration of step (c) was conducted at 55±5° C. The banana peel extract adopted in accordance with the present invention can be a concentrated extract solution provided by step (c), or a dry matter provided by step (d). In step (d), the concentrated extract solution can be dried by way of such as freeze-drying or spray-drying. To achieve an extraction efficiency as high as possible, optionally, the banana peel can be repeatedly extracted with the same or different extraction solvents prior to step (b) and the extracts thus obtained are combined to provide the crude extract solution for use in step (b); also, step (b), step (c), and/or the cycle of other optional operations described above can be repeated.

The composition provided in accordance with the present invention can be a pharmaceutical composition or a food composition. The pharmaceutical composition provided in accordance with the present invention is used for at least one of treating insomnia, treating diseases related to neurometabolic disorder, and preventing diseases related to neurometabolic disorder. Preferably, the pharmaceutical composition is used for treating insomnia. The food composition provided in accordance with the present invention is used for at least one of ameliorating sleep disturbances, regulating appetite, regulating sleep, regulating mood, regulating vasoconstriction, regulating hemostatic function and regulating immune response. Preferably, the food composition is used for ameliorating sleep disturbances.

Depending on the desired purpose, the pharmaceutical composition of the present invention can be provided in any suitable form without particular limitations. For example, the pharmaceutical composition can be administered to a subject in need by an oral or parenteral (such as transdermal) route, but is not limited thereby. Depending on the form and purpose, suitable carriers can be chosen and used to provide the pharmaceutical composition, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form suitable for oral administration, the pharmaceutical composition in accordance with the present invention can comprise any pharmaceutically acceptable carrier that will not adversely affect the desired effects of the active ingredient (i.e., banana peel extract). Examples of suitable carriers include, but are not limited to, water, saline, dextrose, glycerol, ethanol or its analogs, cellulose, starch, sugar bentonite, and combinations thereof. The pharmaceutical composition can be provided in any suitable form for oral administration, such as in the form of a tablet (e.g., dragee), a pill, a capsule, a granule, a pulvis, a fluidextract, a solution, syrup, a suspension, a tincture, etc.

As a dosage form suitable for transdermal administration, the pharmaceutical composition can be provided in a form of a patch, an emulsion, a cream, a gel (such as a hydrogel), a paste (such as a dispersing paste, an ointment), a spray, or a solution (such as a suspension) for external use, but is not limited thereby.

Depending on the need, age, body weight, and health conditions of the subject, the pharmaceutical composition provided in accordance with the present invention can be administered at various frequencies, such as once a day, multiple times a day, or once every few days, etc. The ratio of amount of banana peel extract in the pharmaceutical composition provided in accordance with the present invention can be adjusted depending on the requirements of practical application. In addition, the pharmaceutical composition can optionally further comprise one or more other active ingredient(s) (e.g., hypnotic drugs, antidepressants, and melatonin), or to be used in combination with a medicament comprising one or more other active ingredient(s), to further enhance the effects of the pharmaceutical composition or to increase the application flexibility and adaptability of the preparation thus provided, as long as the other active ingredients will not adversely affect the desired effects of the active ingredients of the present invention (i.e., banana peel extract).

Optionally, the pharmaceutical composition or food composition provided in accordance with the present invention can further comprise a suitable amount of additives, such as a flavoring agent, a toner, or a coloring agent for enhancing the palatability and the visual perception of the pharmaceutical composition or food composition, and/or a buffer, a conservative, a preservative, an antibacterial agent, or an antifungal agent for improving the stability and storability of the pharmaceutical composition or food composition.

The food composition provided in accordance with the present invention can be a health food, a dietary supplement, a functional food, a nutritional supplement food or a special nutritional food, and can be manufactured as dairy products, meat products, breadstuff, pasta, cookies, troche, capsule, fruit juices, teas, sport beverages, nutritional beverages, etc., but is not limited thereby. Preferably the food composition provided in accordance with the present invention is a health food.

Depending on the age, body weight and healthy conditions of the subject, the health food, dietary supplement, functional food, nutritional supplement food and special nutritional food provided by the present invention can be taken at various frequencies, such as once a day, several times a day or once every few days, etc. The amount of the banana peel extract in the health food, dietary supplement, functional food, nutritional supplement food and special nutritional food provided in accordance with the present invention can be adjusted, preferably to the amount that it should be taken daily, depending on the specific population.

The recommended daily dosage, use standards and use conditions for a specific population (e.g., patient with insomnia, patient with depression, and pregnant woman), or the recommendations for a use in combination with another food product or medicament can be indicated on the exterior package of the health food, dietary supplement, functional food, nutritional supplement food and/or special nutritional food provided in accordance with the present invention. Thus, it is suitable for the user to take the health food, dietary supplement, functional food, nutritional supplement food and/or special nutritional food by him- or herself safely and securely without the instructions of a doctor, pharmacist, or related executive. In the food composition provided in accordance with the present invention, the type and related uses of the banana peel extract are all in line with the above descriptions.

The present invention also provides a method for increasing expression of TPH1 gene, DDC gene and/or AANAT gene, comprising administering a composition to a subject in need, wherein the composition comprises an effective amount of banana peel extract. The applied type, applied route, applied form, applied frequency and uses in related application of the composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

The sources of materials used in the following Examples are as follows:
1. Banana: Taiwan.
2. Human neuroblastoma cell (SH-SY5Y): purchased from ATCC, and the product number was CRL-2266.
3. DMEM medium: purchased from Gibco, and the product number was 12100-038.
4. Fetal bovine serum: purchased from Gibco, and the product number was 10438-062.
5. Penicillin/streptomycin: purchased from Gibco, and the product number was 15140-122.
6. RNA Extract Kit: purchased from Geneaid.
7. SuperScript® III Reverse Transcriptase: purchased from Invitrogen.
8. KAPA SYBR FAST qPCR kit: purchased from KAPA Biosystems.
9. Step One Plus system: purchased from ABI.
10. Melatonin direct Saliva ELISA, 96T: purchased from IBL, and the product number was RE54041.
11. Ficoll-Paque Plus: purchased from GE Healthcare.

Example 1: Preparation of Banana Peel Extract

The flesh and peel of banana were separated, and then the banana peel was subjected to an operation comprising the following steps, to provide a banana peel extract:
1. Mixing the banana peel and a extraction solvent (the volume ratio of extraction solvent:banana peel=6:1; the extraction solvent was provided by mixing citric acid with water at a volume ratio of 1:100 (citric acid: water)) for conducting the extraction at 85° C. for 0.5 hour to provide a crude extract solution;
2. Centrifuging the crude extract solution of step 1 at 5000 rpm for 10 minutes, and then filtering the supernatant thus obtained with a 400-mesh filter to provide a filtrate;
3. Concentrating the filtrate by vacuum of step 2 at 55±5° C. to provide a concentrated extract solution; and
4. Freeze-drying the concentrated extract solution of step 3 to provide a dry matter (i.e., the banana peel extract used in the following Examples).

Example 2: Cellular Experiment

Human neuroblastoma cells were seeded in a 6-well plate ($2 \times 10^5$ cells/well) to conduct a cultivation for 24 hours. Thereafter, cells were divided into the control group and extract group (triplicated for each group) and were separately cultivated in the following medium for 6 hours:
1. Control group: a DMEM medium containing 10% fetal bovine serum and 1% penicillin/streptomycin; and
2. Extract group: a medium the same as that of the control group, but additionally added with 15.625 μg/ml banana peel extract obtained from Example 1.

Thereafter, cells of the above groups were harvested and subjected to a RNA extraction with an RNA Extract Kit. The RNA was then transcribed into cDNA with a Reverse Transcriptase. Thereafter, the aforementioned cDNA was subjected to a quantitative polymerase chain reaction (qPCR) by a Step One Plus system and a KAPA SYBR FAST qPCR kit to determine the expression levels of genes related to melatonin (including TPH1, DDC and AANAT) in the cells of each group. Then, the expression level of each gene of the extract group was calculated by using the result of the control group as a basis (i.e., set the expression level of the control group as 1-fold). The results are shown in FIG. 1.

As shown in FIG. 1, as compared to the control group, the expression levels of TPH1, DDC and AANAT genes in the cells of the extract group all significantly higher, wherein the expression level of AANAT gene in the cells of the extract group was even 3.33-fold that of the control group. These results indicate that the banana peel extract in accordance with the present invention is effective in increasing the expression levels of TPH1, DDC and AANAT genes, and thus, can be used for increasing the expression of melatonin and promoting the secretion of melatonin, thereby achieving the effects of treating insomnia and ameliorating sleep disturbances.

Example 3: Human Experiment (3-1) Collection of Samples

Volunteered subjects were recruited (people taking hypnotic drugs, people taking hypoglycemic agent, or pregnant women were excluded) and separated into the following three groups (one person for each group): "person has significant sleep disturbance (hereinafter referred to as "group I")," "person has potential sleep disturbance (hereinafter referred to as "group II")" and "person without sleep disturbance (hereinafter referred to as "group III")." Thereafter, the sleep conditions of the subjects were evaluated. Prior to drinking the beverage containing the banana peel extract in accordance with the present invention, each subject was invited to fill out the sleep questionnaire (i.e., sleep questionnaire at day 0, the questionnaire is depicted in FIG. 5), and the saliva and blood of each subject were collected (i.e., saliva and blood at day 0) for subsequent experiments. Then, the subjects drank beverage containing 200 mg banana peel extract obtained from Example 1 every night (after dinner) for 7 days (i.e., each subject drank the beverage for 7 times). Thereafter, each subject was invited again to fill out the sleep questionnaire (i.e., sleep questionnaire at day 7, wherein the contents were the same as those of the sleep questionnaire at day 0), and the saliva and blood of each subject were also collected (i.e., saliva and blood at day 7) for subsequent experiments.

(3-2) Sleep Disturbance Score

The sleep questionnaires at day 0 and day 7 obtained from 3-1 were analyzed, and the sleep disturbance scores of the subjects of each group were calculated. The basis of sleep disturbance was set at 8 (i.e., if the score of a subject was higher than 8, it represented that the subject had sleep disturbance). The results are shown in FIG. 2.

Figure 2:
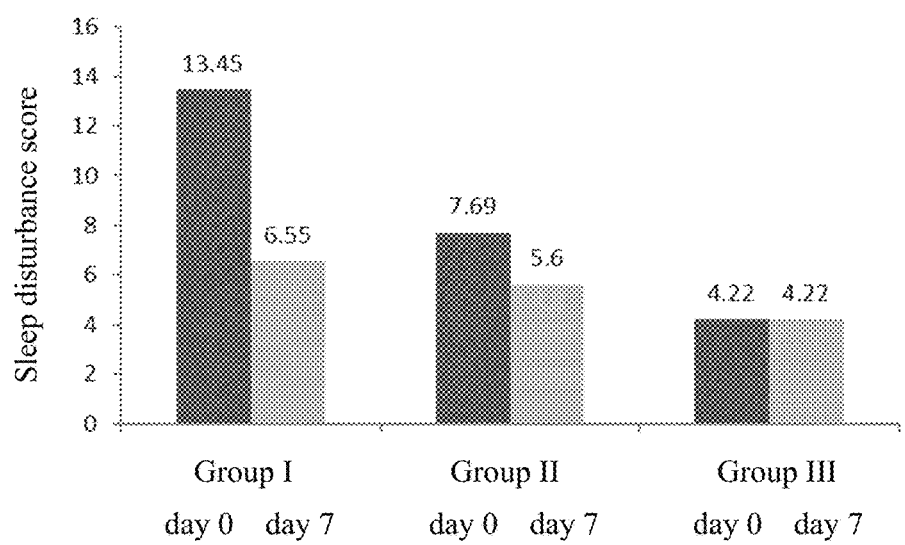
FIG. 2 shows the sleep disturbance scores of group I to group III at day 0 (i.e., the scores prior to drinking banana peel extract) and day 7 (i.e., the scores after drinking banana peel extract for continuous 7 days), wherein the subjects in group I were those having significant sleep disturbance, the subjects in group II were those having potential sleep disturbance, and the subjects in group III were those without sleep disturbance.

As shown in FIG. 2, as compared to day 0, the sleep disturbance scores of the "group I" and "group II" at day 7 both significantly decreased, while the sleep disturbance score of the "group III" did not change significantly. These results indicate that the banana peel extract of the present invention can effectively decrease the sleep disturbance of "person has significant sleep disturbance" and "person has potential sleep disturbance," and will not adversely affect "person without sleep disturbance."

(3-3) Content of Melatonin

The saliva at day 0 and day 7 of each group provided by 3-1 subjected to a test with Melatonin direct Saliva ELISA, 96T to estimate the contents of melatonin in saliva (affected by both the expression and secretion of melatonin). Then, the relative contents of melatonin at day 7 were calculated by using the results at day 0 as a basis (i.e., set the content of melatonin at day 0 as 1-fold). The results are shown in FIG. 3.

Figure 3:
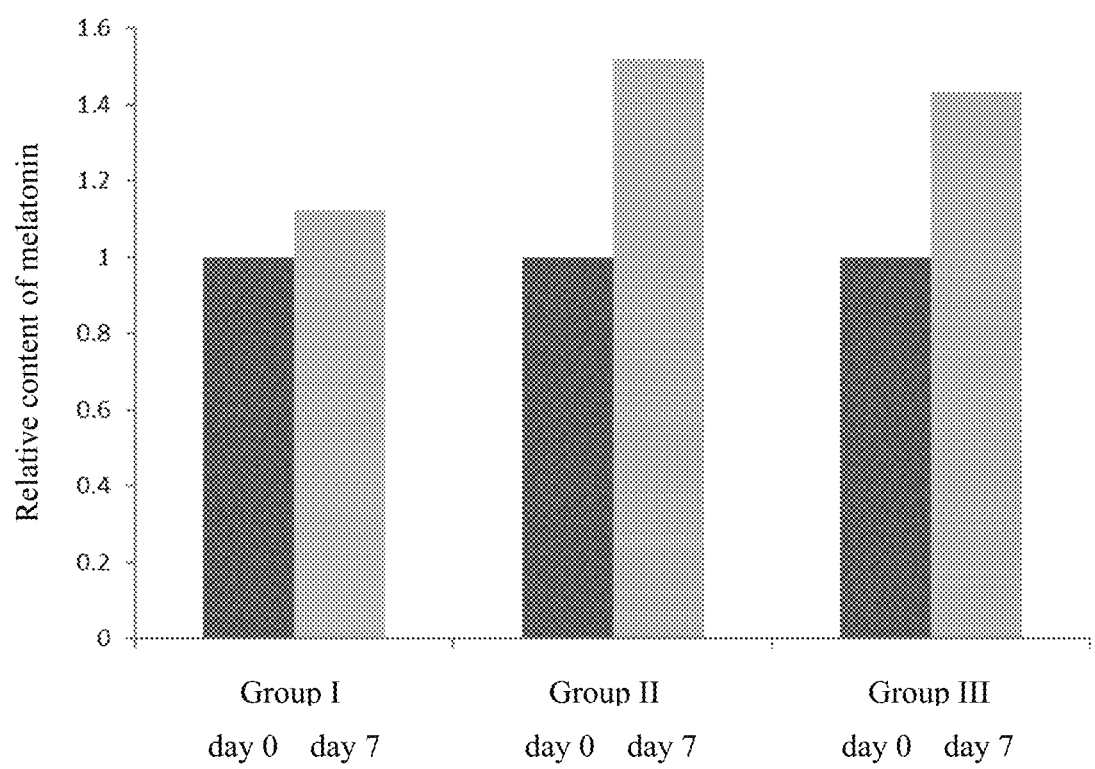
FIG. 3 shows, in comparison with that of the control group, the melatonin content in saliva each of the above group I to group III at day 0 and day 7.

As shown in FIG. 3, as compared to day 0, the contents of melatonin in saliva of the "group I," "group II" and "group III" at day 7 all significantly increased. These results indicate that the banana peel extract can effectively increase the expression of melatonin and promote the secretion of melatonin, and thus, can achieve the effects of treating insomnia and ameliorating sleep disturbances.

(3-4) Expression Levels of Genes Related to Melatonin

The blood at day 0 and day 7 of each group provided by 3-1 were subjected to an isolation with Ficoll-Paque Plus to obtain the peripheral blood mononuclear cells (PBMCs). Thereafter, the expression levels of genes related to melatonin (including TPH1 and AANAT) in the PBMCs of each group were determined by the analyzing method of Experiment 2. Then, the expression level of each gene at day 7 was calculated by using the result at day 0 as a basis (i.e., set the expression level at day 0 as 1-fold). The results are shown in FIG. 4.

Figure 4:
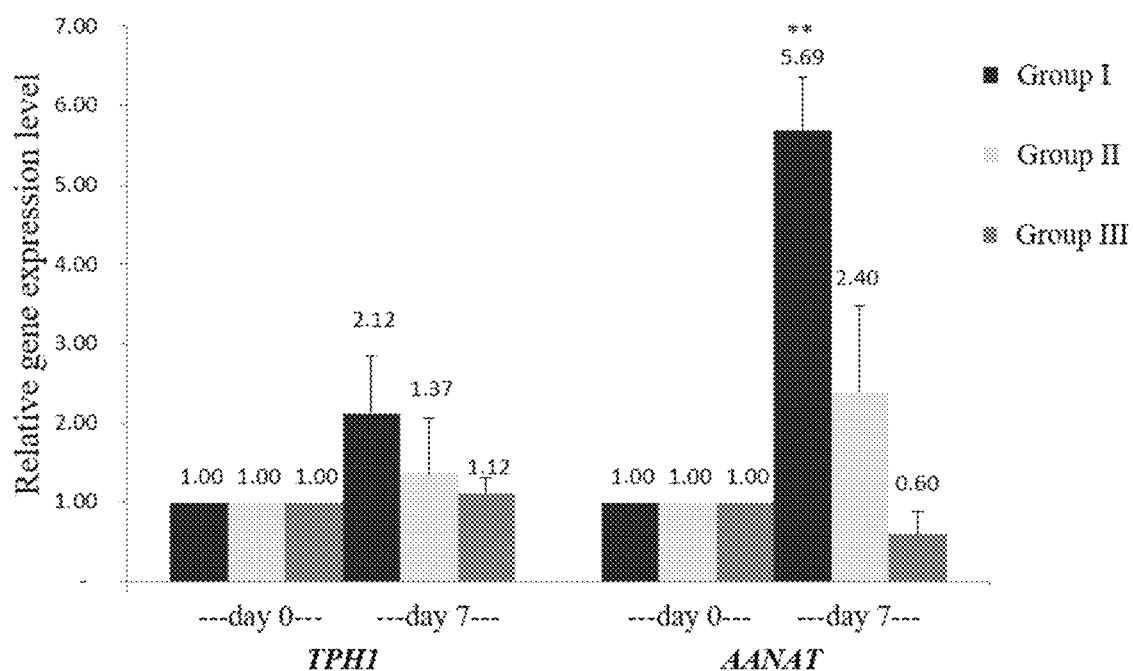
FIG. 4 shows, in comparison with those of the control group, the expression levels of TPH1 gene and AANAT gene in the peripheral blood mononuclear cells of the above group I to group III at day 0 and day 7.

As shown in FIG. 4, as compared to day 0, the expression levels of TPH1 and AANAT genes in the PBMCs of the "group I" and "group II" at day 7 both significantly increased. These results indicate that the banana peel extract is effective in increasing the expressions of TPH1 and AANAT genes in "person with significant sleep disturbance" and "person having potential to with sleep disturbance," and thus, can be used for increasing the expression of melatonin and promoting the secretion of melatonin, thereby achieving the effects of treating insomnia and ameliorating sleep disturbances.

As shown in the above experiments, the banana peel extract is effective in increasing the expression of TPH1, DDC and AANAT genes, and thus, can be used for increasing the expression of melatonin and promoting the secretion of melatonin, and can also be used for at least one of treating insomnia, ameliorating sleep disturbances, treating diseases related to neurometabolic disorder, preventing diseases related to neurometabolic disorder, regulating appetite, regulating sleep, regulating mood, regulating vasoconstriction, regulating hemostatic function and regulating immune response, especially be used for treating insomnia and/or ameliorating sleep disturbances.

What is claimed is:

1. A method for increasing the expressions of TPH1 (Tryptophan hydroxylase 1) gene, DDC (DOPA decarboxylase) gene and/or AANAT (aralkylamine N-acetyltransferase) gene, comprising administering to a subject in need a composition, wherein the composition comprises an effective amount of a banana peel extract, wherein the banana peel extract is a polar solvent extract of banana peel, and the polar solvent contains an acid.

2. The method as claimed in claim 1, which is for increasing the expression of melatonin and/or promoting the secretion of melatonin.

3. The method as claimed in claim 1, which is for at least one of treating insomnia, treating diseases related to neurometabolic disorder, preventing diseases related to neurometabolic disorder, ameliorating sleep disturbances, regulating appetite, regulating sleep, regulating mood, regulating vasoconstriction, regulating hemostatic function, and regulating immune response.

4. The method as claimed in claim 3, which is for treating insomnia.

5. The method as claimed in claim 3, which is for ameliorating sleep disturbances.

6. The method as claimed in claim 3, wherein the composition is administered to the subject by oral administration, transdermal administration, or a combination thereof.

7. The method as claimed in claim 4, wherein the composition is administered to the subject by oral administration, transdermal administration, or a combination thereof.

8. The method as claimed in claim 5, wherein the composition is administered to the subject by oral administration, transdermal administration, or a combination thereof.

* * * * *